United States Patent
Xu et al.

(10) Patent No.: US 8,976,366 B2
(45) Date of Patent: Mar. 10, 2015

(54) SYSTEM AND METHOD FOR MONITORING LED CHIP SURFACE ROUGHENING PROCESS

(75) Inventors: James Jianguo Xu, San Jose, CA (US); Ken Kinsun Lee, Los Altos Hills, CA (US); Rusmin Kudinar, Fremont, CA (US); Ronny Soetarman, Fremont, CA (US); Hung Phi Nguyen, Santa Clara, CA (US); Zhen Hou, Fremont, CA (US)

(73) Assignee: Zeta Instruments, Inc., San Jose, CA (US)

( * ) Notice: Subject to any disclaimer, the term of this patent is extended or adjusted under 35 U.S.C. 154(b) by 115 days.

(21) Appl. No.: 13/494,949

(22) Filed: Jun. 12, 2012

(65) Prior Publication Data

US 2012/0327414 A1    Dec. 27, 2012

Related U.S. Application Data

(60) Provisional application No. 61/501,696, filed on Jun. 27, 2011.

(51) Int. Cl.
*G01B 11/30*     (2006.01)
*G01J 3/28*     (2006.01)
(Continued)

(52) U.S. Cl.
CPC ........... *G01J 3/2823* (2013.01); *G02B 21/0092* (2013.01); *G01J 3/0208* (2013.01); *G01J 3/0218* (2013.01); *G01N 21/274* (2013.01); *G01N 21/55* (2013.01)
USPC ....................................................... 356/600

(58) Field of Classification Search
CPC ..... G01N 21/274; G01N 21/55; G01J 3/2823; G01J 3/0208; G01J 3/0218; G02B 21/0092

USPC ............. 356/72, 73, 445, 600, 603, 300, 303, 356/322, 326, 327; 250/559.07, 559.09, 250/559.22; 382/108, 141, 154; 359/368–398

See application file for complete search history.

(56) References Cited

U.S. PATENT DOCUMENTS 4,511,800 A     4/1985   Harbeke et al.
6,121,616 A *   9/2000   Trigg ....................... 250/339.07
(Continued)

OTHER PUBLICATIONS

M. Modreanu, M. Gartner, E. Aperathitis, N. Tomozeiu, M. Androulidaki, D. Cristea, Paul Hurley, "Investigation on preparation and physical properties of nanocrystalline Si/SiO2 superlattices for Si-based light-emitting devices" Physica E: Low-dimensional Systems and Nanostructures, vol. 16, Issues 3-4, Mar. 2003, pp. 461-466.*

*Primary Examiner* — Tri T Ton
*Assistant Examiner* — Willie Merrell, II
(74) *Attorney, Agent, or Firm* — Bever, Hoffman & Harms, LLP (57) ABSTRACT

A measurement system for monitoring an LED chip surface roughening process is described. A reflective illuminator can run reflectance measurements. A vertical positioning means can adjust a distance between an objective lens and an industrial sample. A horizontal positioning means can move objects in XY plane, and is specifically configured to hold the industrial sample and a reference sample. An optical sensor can acquire images of the industrial sample. A spectrometer can acquire reflectance spectrums of the industrial sample and the reference sample. A processor can control these components. The processor can perform deskew, and calculate an average reflectance and an oscillation amplitude from the reflectance spectrums of the industrial sample.

42 Claims, 10 Drawing Sheets

(51) Int. Cl.
    *G02B 21/00* (2006.01)
    *G01J 3/02* (2006.01)
    *G01N 21/27* (2006.01)
    *G01N 21/55* (2014.01)

(56) References Cited

U.S. PATENT DOCUMENTS

| | | |
|---|---|---|
| 6,452,678 B2 | 9/2002 | Thakur et al. |
| 7,563,625 B2 | 7/2009 | Tran et al. |
| 7,729,049 B2 | 6/2010 | Xu et al. |
| 7,944,609 B2 | 5/2011 | Xu et al. |
| 8,174,762 B2 | 5/2012 | Xu et al. |
| 8,184,364 B2 | 5/2012 | Xu et al. |
| 2007/0114511 A1 | 5/2007 | Kim et al. |
| 2008/0297765 A1* | 12/2008 | Weidner et al. .......... 356/51 |
| 2009/0195869 A1* | 8/2009 | Kim et al. .......... 359/386 |
| 2009/0219381 A1* | 9/2009 | Ayala .......... 348/43 |
| 2009/0315055 A1 | 12/2009 | Tamboli et al. |
| 2010/0051822 A1* | 3/2010 | Harrison .......... 250/372 |
| 2012/0019626 A1 | 1/2012 | Hou et al. |

\* cited by examiner

SYSTEM AND METHOD FOR MONITORING LED CHIP SURFACE ROUGHENING PROCESS

RELATED APPLICATIONS

This application claims priority of U.S. Provisional Patent Application 61/501,696, entitled "SYSTEM AND METHOD OF MONITORING LED CHIP SURFACE ROUGHENING PROCESS" filed Jun. 27, 2011.

BACKGROUND OF THE INVENTION

1. Field of the Invention

The present invention relates to a surface measurement system and more particularly to an optical three-dimensional (3D) imaging system and method for monitoring a surface roughening process in light emitting diode (LED) chip manufacturing.

2. Related Art

In recent years, high brightness LEDs (HBLEDs) have found increasing uses in automotive, traffic, and industrial lighting as well as in display applications. One key performance parameter of a HBLED is its overall efficiency. This parameter is determined by two factors: 1) the internal efficiency of its active layer in converting electric energy to light when the LED is energized and 2) the light extraction efficiency, i.e. the fraction of light that is able to escape the chip through all exposed surfaces. Because the internal efficiency has been improved to approach the theoretical limit, emphasis now has been placed on improving the light extraction efficiency. One approach to improve the light extraction efficiency roughens a surface of the HBLED during manufacturing. The roughening can be done using photoelectrochemical (PEC) oxidation and etching of an n-gallium nitride (n-GaN) layer, which is described, for example, in U.S. Publication 2009/0315055, entitled "Photoelectrochemical Roughening Of P-Side-Up GaN-Based Light Emitting Diodes", and filed by Adele Tamboli et al.

For a HBLED manufacturer, monitoring this PEC surface roughening process is very important. Currently, there are several types of systems that can measure PEC roughened LED surfaces. One type of system, which is described in U.S. Pat. No. 7,563,625, entitled "Method Of Making Light-Emitting Diodes (LEDs) With Improved Light Extraction By Roughening", and issued to Chuong Anh Tran et. al. on Jul. 21, 2009, uses a scanning electron microscope (SEM) to measure such roughness. Although the SEM provides high resolution images of a surface, it is difficult to obtain quantitative vertical dimensions unless a sample is cut and a cross-sectional measurement is performed. Because the SEM is generally a destructive method, it is undesirable in a commercial manufacturing environment. In addition, even if not destructive, the SEM has to operate in a vacuum environment, thereby resulting in relatively low throughput.

Another type of system, which is described in U.S. Publication 2007/0114511, entitled "III-Nitride Compound Semiconductor Light Emitting Device", and filed by Chang-Tae Kim et. al., uses an atomic force microscope (AFM) to monitor the surface roughening process. Although the AFM is capable of generating very high resolution images, it is difficult to obtain repeatable surface roughness results. Moreover, the AFM result is influenced by the condition of its tip, which needs to be replaced frequently to ensure accuracy. Yet further, the AFM requires highly trained operators, and is highly susceptible to environmental noise and vibrations. Finally, the AFM semi-contact method is somewhat destructive. Therefore, the use of the AFM is also not a commercially viable method for in-process surface roughness monitoring.

Yet another type of system, which is described in U.S. Pat. No. 4,511,800, entitled "Optical Reflectance Method For Determining The Surface Roughness Of Materials In Semiconductor Processing", and issued to Gunther Harbeke et. al. on Apr. 16, 1985, and U.S. Pat. No. 6,452,678, entitled "Reflectance Method For Evaluating The Surface Characteristics Of Opaque Materials", and issued to Randhir Thakur et. al. on Sep. 17, 2002, uses optical reflectance-based methods instead of high resolution imaging to monitor surface roughness (e.g. for silicon wafers). Although these optical reflectance-based methods are fast and non-destructive, they do not quantify the raw reflectance data into useful information about a PEC roughened LED surface, nor do they adequately address the need for LED production process monitoring.

Therefore, a need arises for a non-destructive method that is fast, easy to use, and relatively inexpensive to implement to monitor PEC surface roughening in HBLED manufacturing.

SUMMARY OF THE INVENTION

A measurement system for monitoring a light emitting diode (LED) chip surface roughening process is described. This measurement system includes an objective lens, a reflective illuminator, vertical and horizontal positioning means, an optical sensor, a spectrometer, and a processor. The reflective illuminator can be configured to run reflectance measurements. The vertical positioning means can adjust a distance between the objective lens and an industrial sample, which includes an LED chip. The horizontal positioning means can move objects in XY plane, and is specifically configured to hold the industrial sample and a reference sample. The optical sensor is capable of acquiring images of the industrial sample. The spectrometer is capable of acquiring reflectance spectrums of the industrial sample and the reference sample. The processor can control the illuminator, the vertical positioning means, the horizontal positioning means, the optical sensor, and the spectrometer. The processor is configured to acquire reference data from the reference sample and to perform deskew, and to calculate an average reflectance and an oscillation amplitude from the reflectance spectrums of the industrial sample.

Another measurement system for monitoring a light emitting diode (LED) chip surface roughening process is described. This measurement system includes an objective lens, an illuminator, a positioning means, an optical sensor, a spectrometer, and a processor. The illuminator can be configured to selectively run a surface reflectance measurement mode and at least one of a regular 3D imaging mode and a polarized light 3D imaging mode. The positioning means can adjust a distance between the objective lens and a sample at a plurality of Z steps. The optical sensor can be configured to acquire images of the sample at each Z step. The spectrometer can be configured to acquire reflectance spectrums based on the images. The processor can control the illuminator, the positioning means, the optical sensor, and the spectrometer.

Yet another measurement system for monitoring a light emitting diode (LED) chip surface roughening process is described. This measurement system includes a turret, a reflective illuminator, vertical and horizontal positioning means, an optical sensor, a spectrometer, and a processor. The turret can include an objective lens. The reflective illuminator can be configured to selectively run a surface reflectance measurement mode and a polarizing light 3D imaging mode. The vertical positioning means can adjust a distance between the objective lens and an industrial sample at a plurality of Z steps. The horizontal positioning means can move objects in XY plane, and is specifically configured to hold the industrial sample and a reference sample. The optical sensor can be capable of acquiring images of the industrial sample at each Z step and of the reference sample at a Z step. The spectrometer can be capable of acquiring reflectance spectrums of the industrial sample and the reference sample. The processor can control the turret, the illuminator, the vertical positioning means, the horizontal positioning means, the optical sensor, and the spectrometer. The processor can be configured to perform deskew, and to calculate an average reflectance and an oscillation amplitude from the reflectance spectrums.

In one embodiment, the objective lens has 5× or lower magnification. The reflective illuminator can include at least one broadband white light LED source. The vertical positioning means can include a motorized Z stage. The horizontal positioning means can include a motorized XY stage. The reference sample can be a polished bare silicon substrate. The optical sensor can include a CCD camera. The spectrometer can be configured to collect reflectance data between 430 nm and 750 nm. The processor can be part of a PC.

In another embodiment, the objective lens can have 5× or lower magnification in the surface reflectance measurement mode, but 100× or higher magnification in the polarizing light 3D imaging mode. The reflective illuminator can be configured to switch between the surface reflectance measurement mode and the polarizing light 3D imaging mode automatically.

Methods of providing these measurement systems are also described.

DETAILED DESCRIPTION OF THE DRAWINGS

Figure 1A:
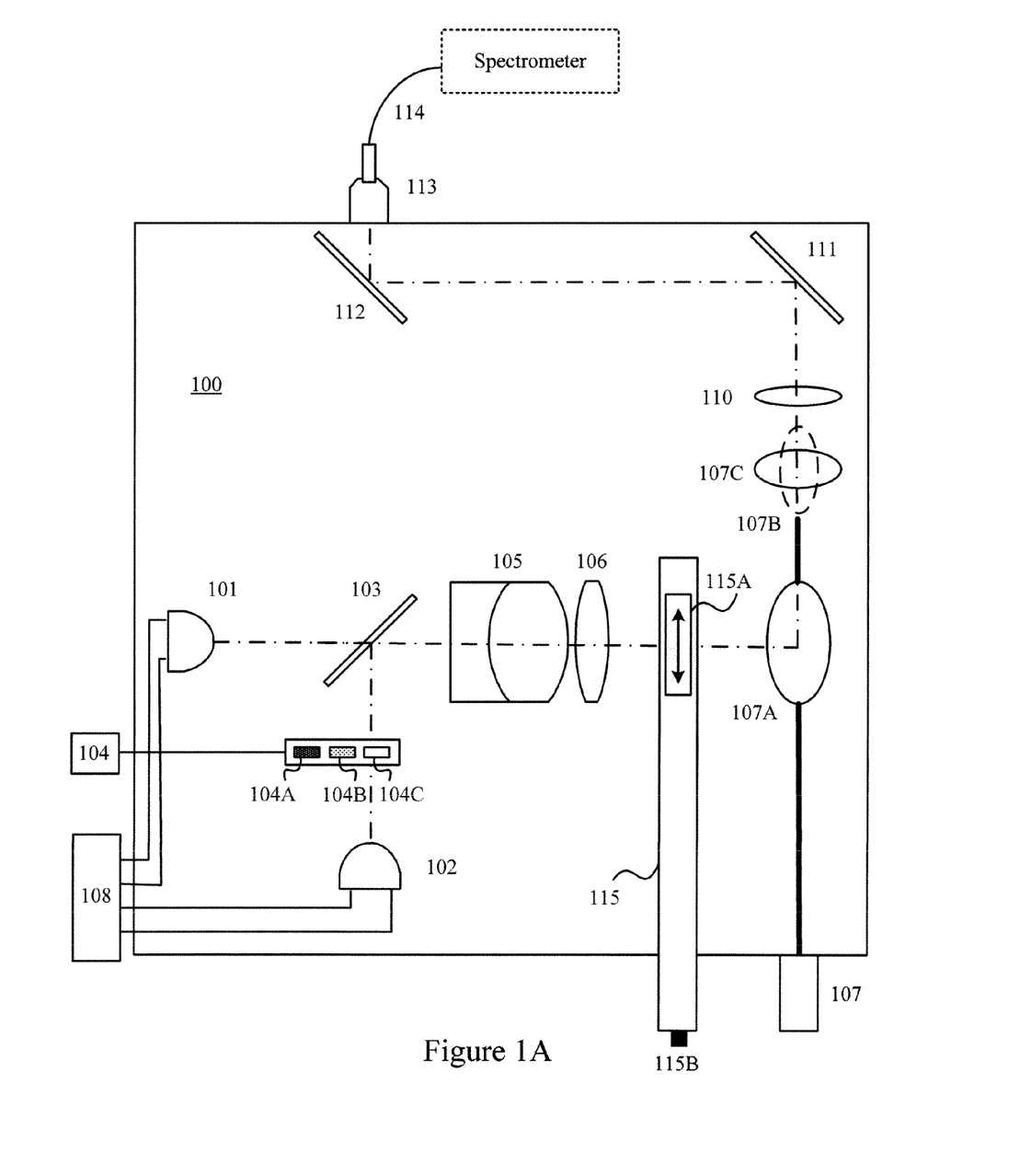
FIG. 1A is a diagram illustrating an illuminator used in a 3D surface measurement system.

FIG. 1A is a diagram illustrating an illuminator 100 used in the 3D surface measurement system of the present invention. Illuminator 100 includes two light sources 101 and 102, which respectively generate first and second light paths (shown by the dot-dashed lines) that define the basic 3D imaging mode of operation of the system. In one embodiment, light sources 101 and 102 are high brightness white color light emitting diodes (LEDs). However, other light sources, such as halogen lamps, fiber coupled lights, lasers, etc., can also be used and are within the scope of this invention.

Both first and second light paths share several components, i.e. a first beam-splitter 103, an achromat doublet lens 105, a double convex lens 106, and a second beam-splitter 107A. Note that other types of lenses can also be used and are within the scope of this invention. In this embodiment, beam-splitter 107A is mounted on a linear slider 107 positioned in the light paths, as are two other beam-splitters 107B and 107C (described below). In this embodiment, patterned articles 104A and 104B are mounted on a linear slider 104, which is positioned in the second light path.

The optical components of illuminator 100 are mounted inside a dark enclosure with two openings (not shown): a top opening and a bottom opening. The top opening is above beam-splitter 107A, whereas the bottom opening is below beam-splitter 107A. These two openings allow light from the first and second light paths to interact with other system components that are external to illuminator 100 (shown, for example, in FIGS. 2, 6, and 7, described below). A multi-pin connector 108 is coupled to light sources 101 and 102 via electrical wires for control of those light sources.

Figure 1B:
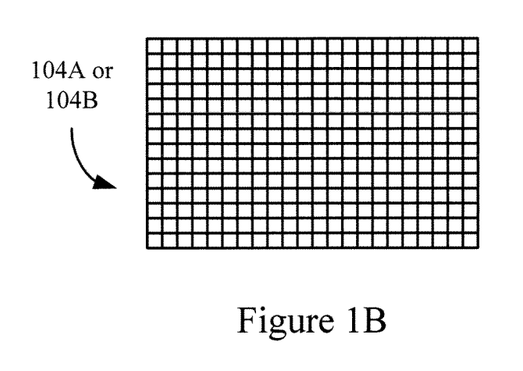
FIG. 1B illustrates an exemplary patterned article.

FIG. 1B illustrates an exemplary patterned article, which could implement one of patterned articles 104A or 104B. In one embodiment, the patterned article includes a transparent material with a two dimensional array of evenly spaced opaque dots formed on one of its surfaces. A different type of pattern, whether regular (e.g. a grid) or random, can also be used as long as the pattern satisfies certain conditions. Specifically, the pattern must (1) have high contrast, (2) be semi-transparent and (3) have a minimum feature size that matches the sampling resolution of an imaging optical sensor used. Note that any suitable material, such as glass, liquid crystal, photographic film, etc., can be used as the transparent material to implement the pattern article and are within the scope of this invention.

Notably, the patterned surface of the patterned article is located at the effective focal plane of the lens group consisting of lenses 105 and 106. As described in reference to FIG. 1C, the patterned article can be used in illuminator 100 to project an image of its pattern onto the focal plane of an objective lens to create enough contrast so that 3D height information of a sample can be obtained.

In one preferred embodiment, patterned articles 104A and 104B have different pattern pitches selected to match specific optical sensor/coupling lens combinations to achieve optimized imaging results. Linear slider 104 can position patterned article 104A, patterned article 104B, or a through-hole 104C in the second light path. Note that using through-hole 104C can be useful in Nomarski or polarized light imaging applications when maximum illumination light intensity is called for by combining light from both light sources 101 and 102.

Polarizer assembly 115 fills an open slot (not shown) on one side of illuminator 100. The orientation of polarizer 115A can be adjusted via a thumb knob 115B for polarized light imaging applications. In one embodiment, when used for Nomarski imaging, polarizer 115A can be set at a fixed orientation.

A third light path as illustrated by the dot-dashed lines in the upper half of FIG. 1A is used in the surface reflectance measurement mode of operation. In this mode, linear slider 107 is positioned so that only beam-splitters 107B and 107C (and not beam-splitter 107A) are in the illumination light path. In this configuration, light from light source 101 passes through beam-splitter 103, lenses 105 and 106, and is directed by beam splitter 107B to travel downward through an objective lens (see, e.g. FIG. 1C) to a sample. After the light hits the sample surface, the light reflects back through the objective lens and beam splitter 107B, and is directed by beam splitter 107C to travel horizontally towards a focusing lens 110. Two mirrors 111 and 112 reflect the converged beam from lens 110 to make two 90-degree turns. The converged beam focuses near the exit of connector 113, which then enters fiber 114 and is collected by a spectrometer (not shown in FIG. 1A) located at the other end of fiber 114.

Figure 2:
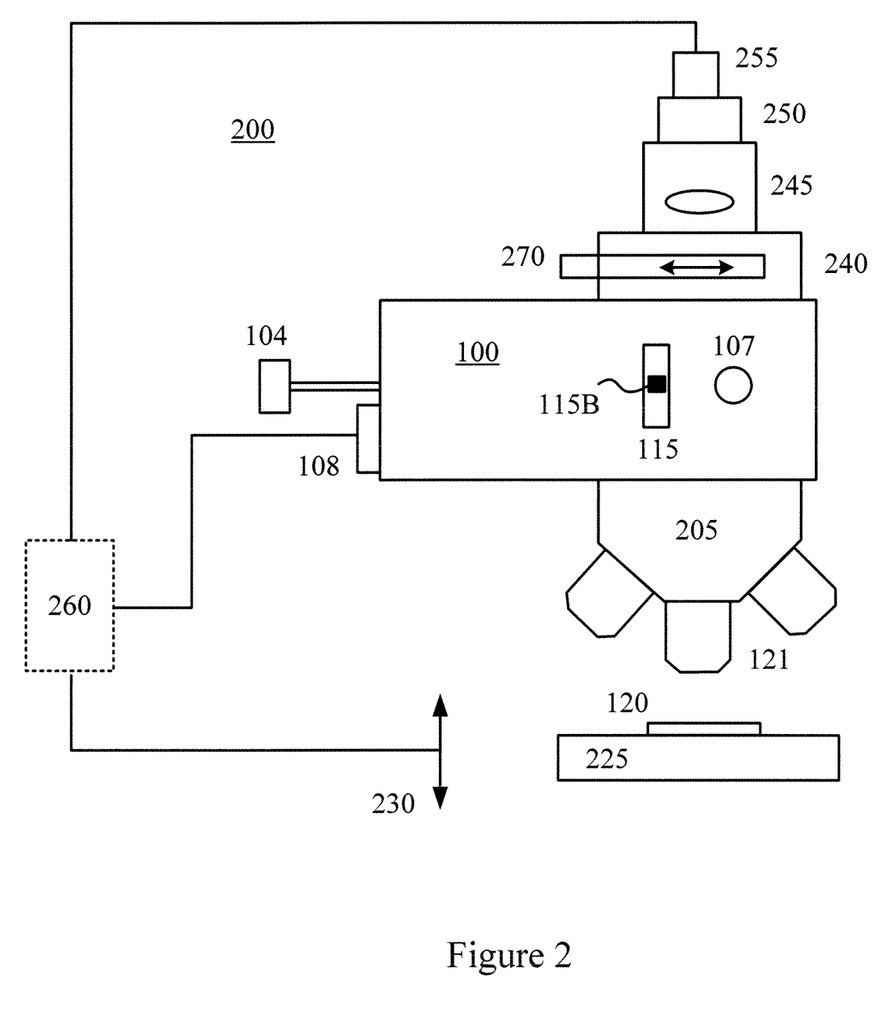
FIG. 2 illustrates an exemplary 3D surface measurement system.

FIG. 2 illustrates an exemplary 3D surface measurement system 200 in accordance with the present invention. Illuminator 100, which is shown in side view, provides reflected illumination in this embodiment and therefore is called a reflective illuminator. For simplicity, only components of illuminator 100 visible from the outside are shown in FIG. 2, wherein internal components of illuminator 100 are shown in and described in reference to FIG. 1A. Note that components having the same reference numerals are the same even though shown in multiple drawings.

In system 200, objective lens 121 is mounted on a turret 205. Turret 205 is mounted directly below the bottom opening of illuminator 100. A positioning means 230 is provided to change the relative position between a sample 120 and objective lens 121. As a result, different features on the sample can be brought into focus of objective lens 121. A manual or motorized XY stage 225 can be incorporated into system 200 to move sample 120 in a horizontal plane. In a preferred embodiment, positioning means 230 is either a motorized Z stage or a motorized Z stage and a piezo-Z stage combination. In other embodiments, the relative position between sample 120 and objective lens 121 can be varied using other components. For example, objective lens 121 could be mounted on a piezoelectric actuator. In such an arrangement, sample 120 would remain stationary while objective lens 121 moves up and down. It is understood by those skilled in the art that these variations are within the scope of this invention. A tube lens 245, an optical sensor coupler 250, and objective lens 121 in combination yield an image of sample 120 on an optical sensor 255. In the preferred embodiment, optical sensor 255 is either a charge-coupled device (CCD) or a complementary metal-oxide-semiconductor (CMOS) camera.

A processor 260 can be connected to various components of system 200, thereby providing configurable and/or automatic control of positioning means 230, illuminator 100, a spectrometer (not shown), and optical sensor 255. Processor 260 can also analyze data from optical sensor 255 and then create a 3-D image of the sample. In the preferred embodiment, processor 260 can form part of a personal computer.

Figure 1C:
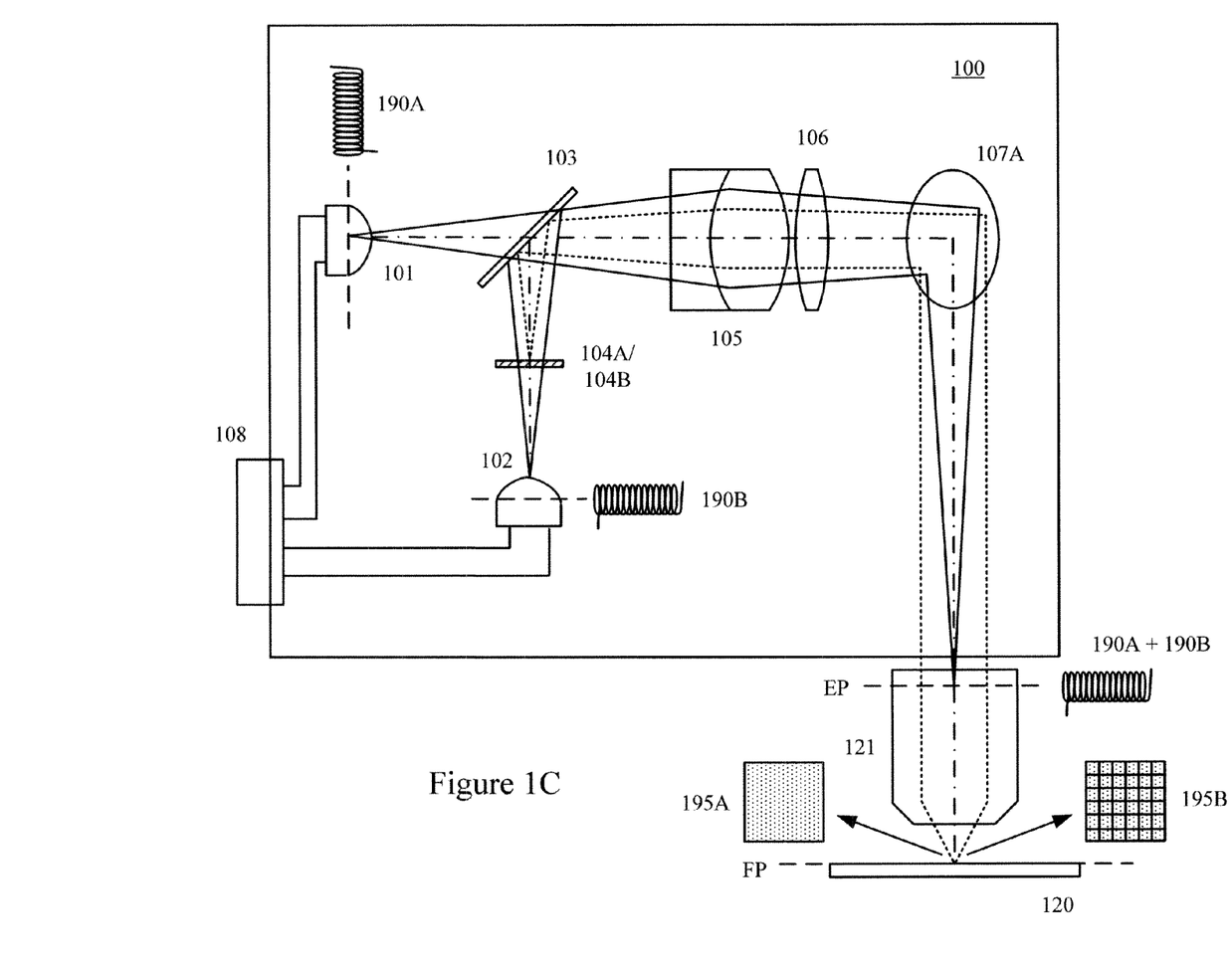
FIG. 1C is a diagram illustrating some of the components of the illuminator of FIG. 1A, an objective lens, a sample, and ray tracings.

There are three modes of operations associated with system 200: regular 3D imaging, polarized light 3D imaging, and surface reflectance measurement. In regular 3D imaging mode, polarizer 115A is pulled out of the imaging optical path, as is an analyzer 270, which is mounted on a tube lens adaptor 240. Referring also to FIG. 10 (which shows a combination of top and side views for illustration purposes), when light source 101 or 102 is turned on and beam-splitter 107A is in the illumination light path, then the lens group formed by lenses 105 and 106 projects an image of the actual light source (e.g. light source 190A or light source 190B) onto the entrance pupil (EP) of an objective lens 121 (shown using the solid line ray tracing), thereby ensuring uniform illumination on a sample 120 (images 195A and 195B having a dot pattern representing the sample for illustration purposes). In contrast, when light source 102 is turned on, and beam-splitter 107A and one of patterned articles 104A or 104B is in the illumination light path, then the lens group formed by lenses 105 and 106 in conjunction with objective lens 121 projects an image of the pattern on patterned article 104A or 104B onto the focal plane (FP) of objective lens 121 (shown using the dotted line ray tracing).

In polarized light 3D imaging mode, both polarizer 115A and analyzer 270 are inserted into the light path, and the transmission axis of polarizer 115A is adjustable via thumb knob 115B. After light from light source 101 passes through polarizer 115A, beamsplitter 107A directs the resulting linearly polarized light waves downward to objective 121. Objective 121 focuses the light waves onto the surface of sample 120. If the sample surface contains both polarization active and inactive regions, the reflected wavefronts emanating from the polarization active region will have their polarization orientation altered while those from the polarization inactive region will not.

The reflected wavefronts are gathered by objective 121, travel upward through beamsplitter 107A, and then encounter analyzer 270, which is positioned with its transmission axis nearly orthogonal to at of polarizer 115A. Wavefront components that are filtered by analyzer 270 pass through tube lens 245 and optical sensor coupler 250, and subsequently form a polarized light image on optical sensor 255. Because light reflected from the polarization active region has a higher transmission rate through analyzer 270 than that of light from the polarization inactive region, features with different polarization properties can be easily distinguished in the image. In polarized light imaging mode of operation, there are cases where more illumination light than either one of the two light sources in FIG. 1A can provides is called for. When this happens, linear slider 104 can be positioned with through-hole 104C in front of light source 102. As a result, light from both 101 and 102 can be combined to illuminate sample 120, which results in maximum intensity for polarized light imaging application.

The operation modes described in the previous paragraphs are for 3D imaging. When light source 101 is turned on and beam splitter 107B is in the illumination light path, the system is operating in the surface reflectance measurement mode. In this mode, polarizer 115A is pulled out of the imaging optical path, as is analyzer 270. Illumination light from light source 101 passes through lenses 105 and 106, and travels downward towards objective 121 upon hitting beam-splitter 107B. The light beam is focused by objective 121 into a small spot on sample surface 120. The reflected light retraces the path of the incoming light to beam-splitter 107B, passes through beam-splitter 107B, makes a 90-degree turn upon hitting beam splitter 107C to travel horizontally towards focusing lens 110. After hitting lens 110, the converging beam makes two 90-degree turns upon hitting mirrors 111 and 112, and focuses near the exit of connector 113. The focused light beam then enters fiber 114 and is collected by a spectrometer, which is located at the other end of fiber 114. For each measurement, data is collected on the sample under investigation as well as on a known standard such as a polished silicon wafer. Processor 260 can analyze the reflectance spectrum provided by the spectrometer and calculates several parameters related to surface reflectance of roughened LED surfaces. These parameters will be discussed in detail later.

U.S. Pat. Nos. 7,729,049, 7,944,609, 8,174,762, and 8,184,364, which are incorporated by reference herein, teach two-pass and one-pass 3D image acquisition processes that can be used in the present invention. For example, referring to FIGS. 1A and 2, in a regular 3D imaging mode of operation, a one-pass 3D image acquisition process can be used. Specifically, positioning means 230 can be controlled to move sample 120 from a pre-determined start position away from objective lens 121 through a set of pre-determined Z steps. At each Z step, processor 260 turns light source 102 on and light source 101 off (hereinafter referred to as Pattern ON). As a result, an image of patterned article 104A or 104B is projected onto the focal plane of objective lens 121, and optical sensor 255 captures and saves a first image of the sample. Then, processor 260 turns light source 101 on and light source 102 off (hereinafter referred to as Pattern OFF), and optical sensor 255 captures and saves a second image of the sample. This process repeats itself until all the Z steps have been taken. When done, processor 260 analyzes the first and second image set to create a 3-D image.

In the polarizing 3D imaging mode of operation, the aforementioned one-pass 3D imaging acquisition process is slightly modified. First, a live image of a sample is observed in focus while adjusting thumb knob 115B, i.e. adjust the orientation of polarizer 115A, until the contrast of the live image is at its best. Then, positioning means 230 can be controlled to move sample 120 from a pre-determined start position away from objective lens 121 through a set of pre-determined Z steps. At each Z step, processor 260 keeps light source 101 on and light source 102 off (i.e. Pattern OFF), and optical sensor 255 captures and saves an image of the sample. This process repeats itself until all the Z steps have been taken. When done, processor 260 analyzes the saved image set to create a 3-D image.

3D imaging is a direct way of observing a PEC roughened LED chip surface. However, its effectiveness is limited by the resolution of an imaging system. For the 3D imaging system described herein, an exemplary resolution limit is about 0.4 μm. Besides 3D imaging, there is an indirect way of gauging surface roughness, which is to measure surface reflectance.

Figure 3:
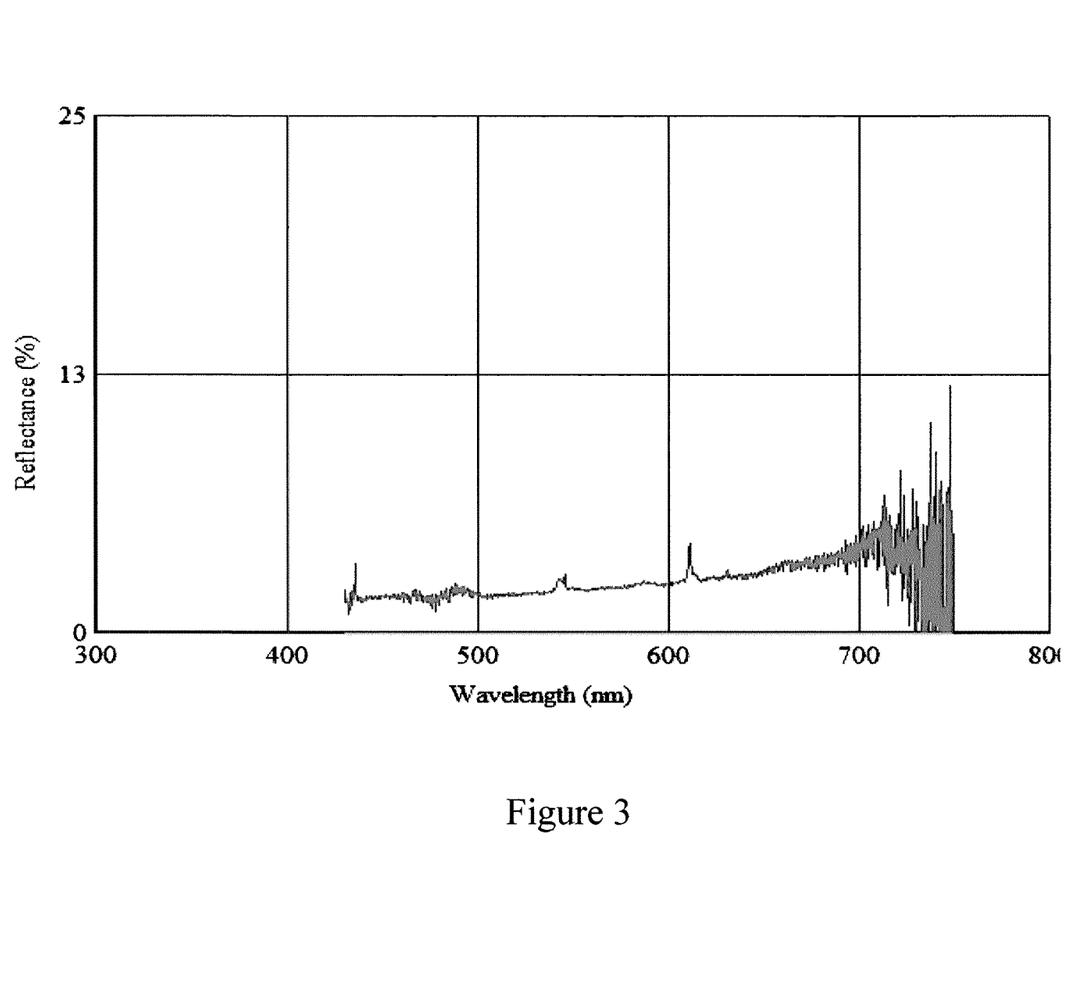
FIGS. 3 and 4 illustrate the measured surface reflectance of two photoelectrochemical roughened LED chips.
Figure 4:
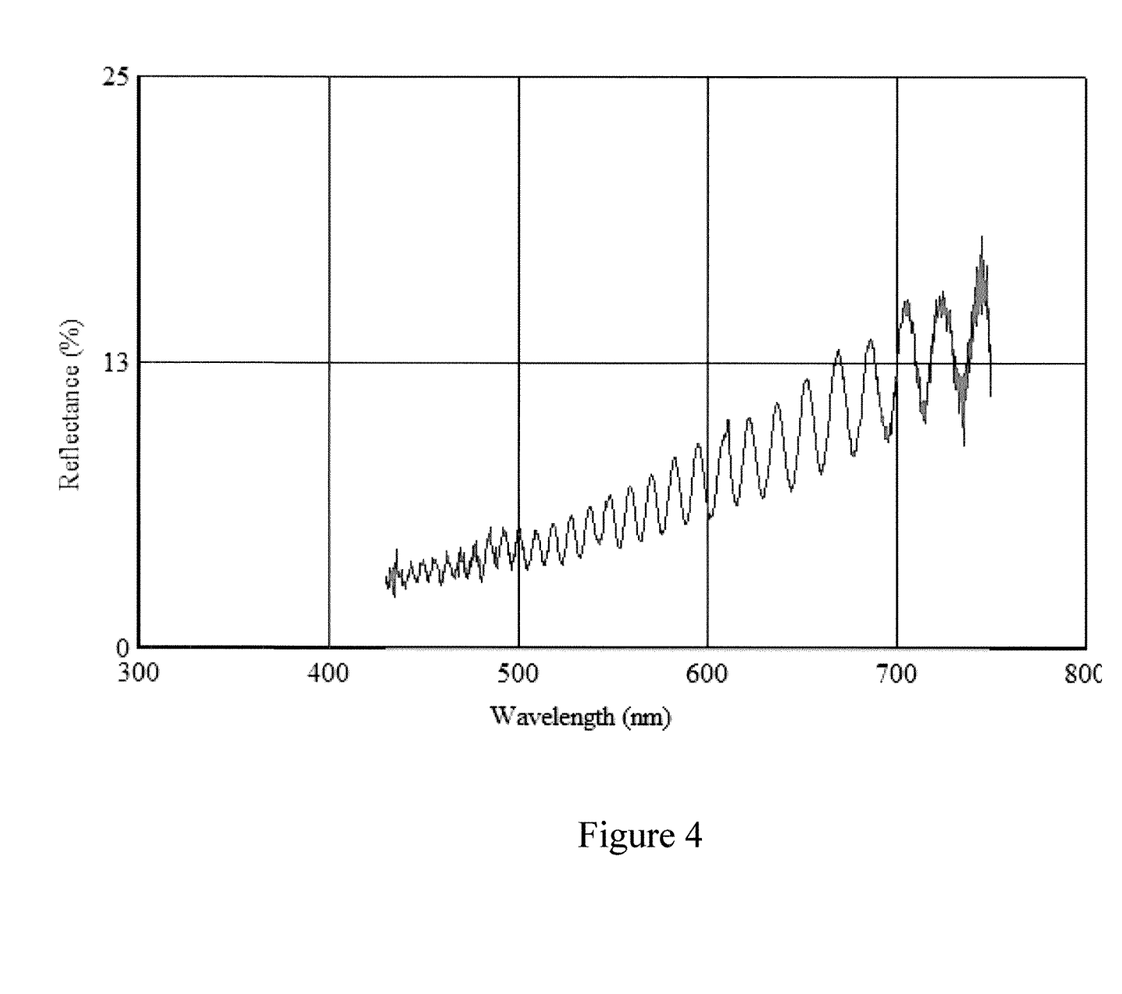

FIGS. 3 and 4 illustrate the measured surface reflectance of PEC roughened LED chips A and B, respectively. The average reflectance within the wavelength range from 430 nm to 750 nm for chips A and B is 2.7% and 8.0%, respectively. Note that sample B not only has a much higher average reflectance, but also shows a strong oscillation in the reflectance curve. To understand this phenomenon, the reflectance and resulting oscillation of an HBLED structure are now described.

Figure 5:
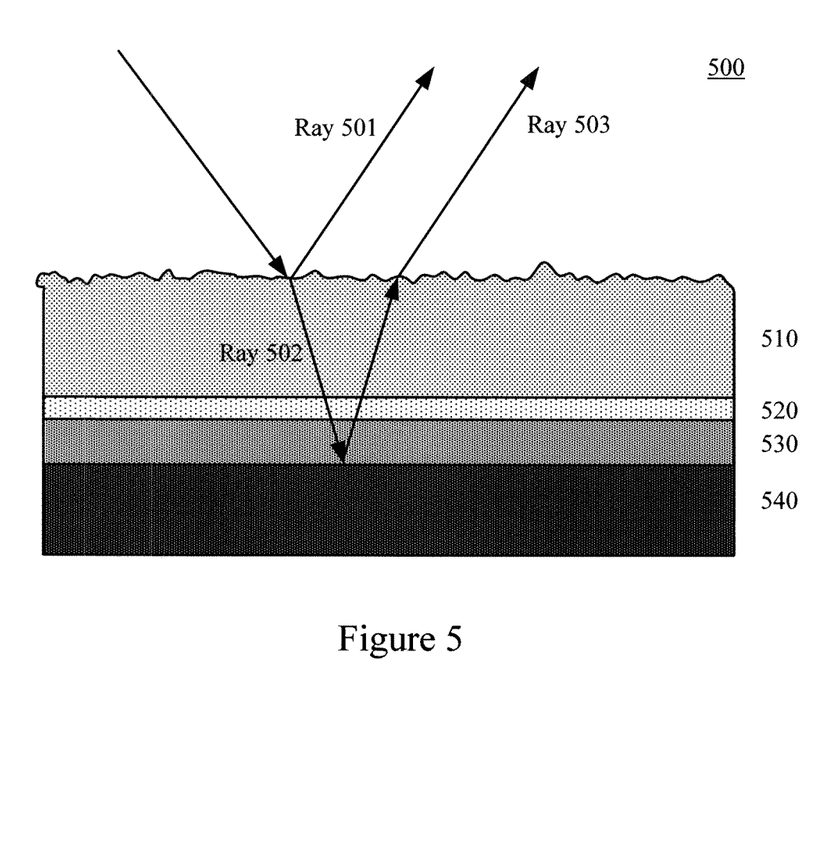
FIG. 5 illustrates a simplified high brightness LED (HBLED) structure.

FIG. 5 illustrates a simplified HBLED structure 500, which includes an n-GaN layer 510 with its top surface roughened to enhance light extraction. HBLED structure 500 further includes a multiple-quantum-well (MQW) active layer 520, a p-GaN layer 530, and a reflector/contact metal layer 540. When energized, MQW active layer 520 generates light for the LED.

In general, when a surface of HBLED structure 500 is illuminated with broadband white light, part of the incident light (shown in FIG. 5 as ray 501) is reflected directly off the top surface while the rest (shown in FIG. 5 as ray 502) undergoes refraction and penetrates into the chip, bounces back from the surface of layer 540, and finally reemerges from the top surface of HBLED structure 500 as ray 503. Rays 501 and 503 (and other rays reflected from any other layers of HBLED structure 500, not shown for simplicity) may create an interference pattern which appears on a reflectance curve as oscillations.

In the case of HBLED structure 500, the rough surface produces random scattering light, thereby minimizing the number of interference fringes that can be formed (i.e. minimizing or even preventing an interference pattern from being formed). When an interference pattern is de minimis, oscillations are not seen in the reflectance curve (see, e.g. FIG. 3, which shows no oscillations in the reflectance curve associated with chip A). In contrast, for a relatively smooth LED chip surface, strong interference fringes can be formed, thereby resulting in oscillations shown in the reflectance curve (see, e.g. FIG. 4, which shows oscillations in the reflectance curve associated with chip B).

With respect to light extraction efficiency, the average reflectance and the oscillation amplitude of the reflectance spectrum are better parameters than surface roughness parameters derived from 3D imaging in predicting the quality of PEC roughened LED chip surfaces. In one preferred embodiment, a low magnification objective (preferably 5× or lower magnification) can be used to collect the sample reflectance spectrum. To calculate the average reflectance, a pre-determined number of pixels of a spectrometer can be analyzed. In one embodiment, certain pixels may be designated as ignored pixels, e.g. the first 10% and the last 10%, thereby leaving 80% of the pixels for analysis. Actual measurement locations can be picked by a user. Exemplary chosen measurement locations are typically those located near the center of a chip. Besides simple arithmetic averages over the entire measured wavelength range, a variety of weighted averages of reflectance and oscillation at one or more wavelengths can be used. Thus, various ways of analyzing surface reflectance curves to monitor PEC roughened LED chip surfaces are within the scope of this invention.

Figure 6A:
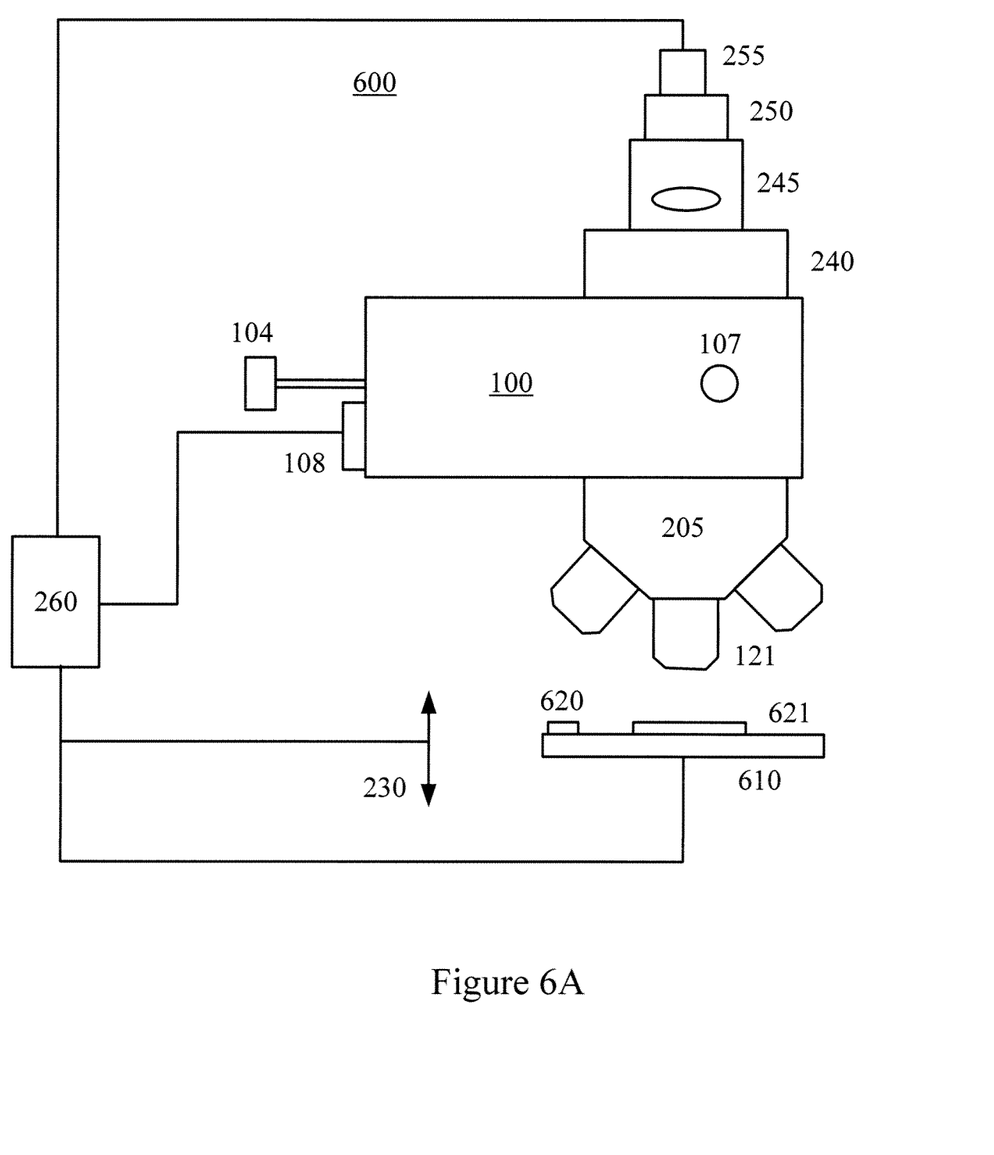
FIG. 6A illustrates a 3D surface measurement system for providing the surface reflectance measurement mode of operation.

In a production environment, throughput and ease of use are two important factors to consider in choosing a measurement system. FIG. 6A illustrates a 3D surface measurement system 600 for providing the surface reflectance measurement mode of operation. Specifically, linear slider 107 is positioned so that beam splitter 107B is in the illumination light path all the time. Polarizer 115A and analyzer 270 are not necessary for system 600 and therefore are pulled out of the illumination path in this embodiment. Illumination light from light source 101 passes through lenses 105 and 106, and travels downward towards objective 121 after hitting beam-splitter 107B. In a preferred embodiment, objective 121 has a magnification of 5× or lower.

Figure 7:
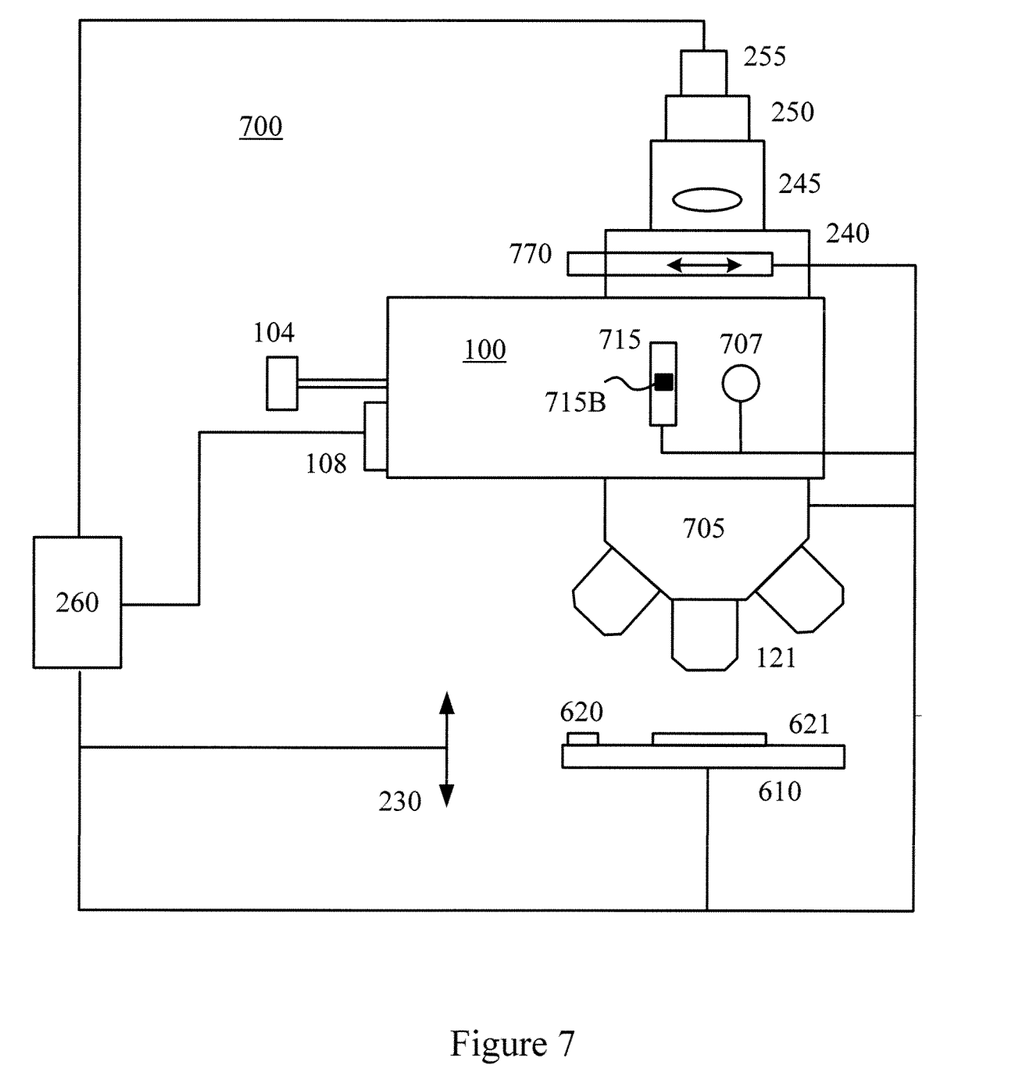
FIG. 7 illustrates another 3D surface measurement system that can automatically provide three modes of operation: a regular 3D imaging mode, a polarized light 3D imaging mode, and a surface reflectance measurement mode.

The light beam is focused by objective 121 into a small spot on the surface of an industrial sample 621 (note that sample 120 is renamed industrial sample 621 in reference to FIGS. 6A and 7 to clearly distinguish it from a reference sample 620). Note that the term "industrial sample" is a sample including features (e.g. at least one of layers, IC patterns, etc.) for industrial application. Therefore, an industrial sample can be an actual wafer, a test wafer, or some other sample with features thereon and/or features therein. The reflected light from industrial sample 621 retraces the path of the incoming light to beam-splitter 107B, passes through beam-splitter 107B, and makes a 90-degree turn upon hitting beam splitter 107C to travel horizontally towards focusing lens 110. After passing through lens 110, the converging beam makes two 90-degree turns by hitting mirrors 111 and 112, and focuses near the exit of connector 113. The focused light beam then enters fiber 114 and is collected by a spectrometer which is located at the other end of fiber 114.

In this embodiment, industrial sample 621 and a piece of polished bare silicon sample, i.e. reference sample 620, are both mounted on a motorized XY stage 610. Reference sample 620 can serve as a reference during reflectance measurement. Because industrial sample 621 is usually in the form of a wafer that includes many LED chips, processor 260 can store a map containing the locations of the measurement spot of each chip on industrial sample 621. The measurement procedure for a typical run is as follow.

Figure 6B:
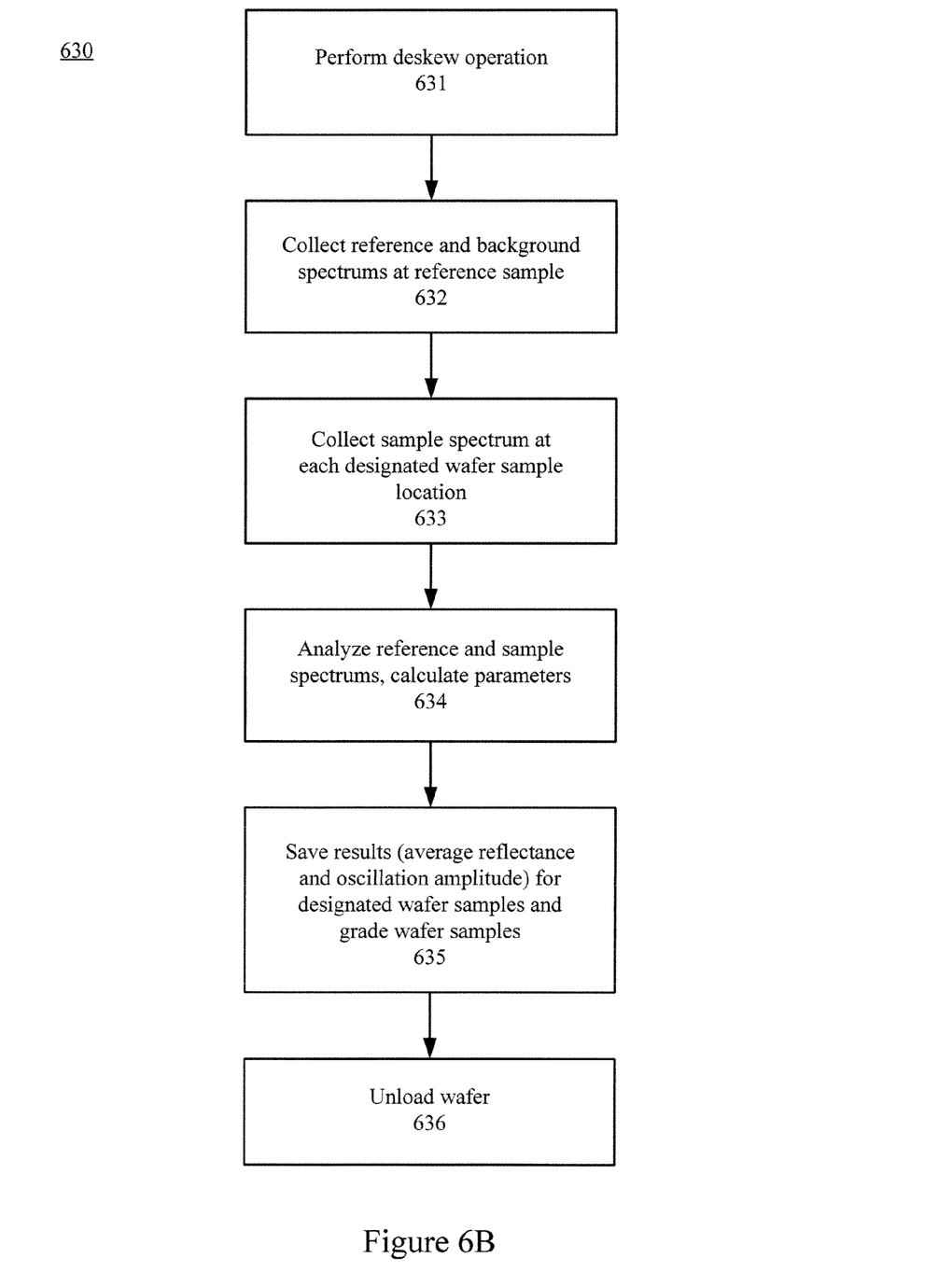
FIG. 6B illustrates an exemplary sequence for performing deskew and analyzing collected spectrums.

An operator places industrial sample 621 on motorized XY stage 610 and turns on a vacuum (not shown) so that industrial sample 621 stays in place during subsequent stage movements. The operator then loads a pre-configured sequence file, which utilizes a chip location map (stored in processor 260) as well as a recipe that defines system parameters. At this point, the operator can push a key to start the sequence. FIG. 6B illustrates an exemplary sequence 630.

In carrying out sequence 630, processor 260 first commands system 600 to perform an alignment process called deskew in step 631. In this alignment process, the XY stage is moved to two pre-defined deskew points on industrial sample 621 based on the chip location map. Preferably these two deskew points are located far away from each other, e.g. on opposite edges of the sample. Using pattern recognition software, processor 260 can automatically center the two pre-defined deskew features in the field of view and record their XY coordinates. These XY coordinates can then be compared to those originally saved in the chip location map to correct for any displacement and rotational offsets incurred during the loading process. The end result of a successful deskew is that system 600 can drive to any pre-defined measurement spot on a chip location map and the desired measurement location will be at the center of field of view.

After deskew, processor 260 commands XY stage 610 to move to the position of reference sample 620 and collects a reference spectrum and a background spectrum in step 632. The background spectrum is collected when the light sources are off (thereby measuring how much of the signal is from the ambient environment). In step 633, processor 260 commands XY stage 610 to move to the deskew corrected nominal location of each chip on industrial sample 621 (or certain pre-selected chips, if so defined in the sequence file). At each chip (i.e. sample), system 600 can collect and save the industrial sample reflectance spectrum. This process can be repeated until every chip that is designated for spectrum analysis is measured. In step 634, processor 260 can analyze the reflectance spectrums saved for reference sample 620 and industrial sample 621, and calculate several parameters such as average reflectance and oscillation amplitude.

In one embodiment, a background spectrum $R_{b(\lambda)}$ can be collected when the light sources are turned off. A reference spectrum $R_{r(\lambda)}$ can also be collected on polished bare silicon. A sample spectrum $R_{s(\lambda)}$ can also be collected from the sample. Using these spectrums, an absolute sample reflectance $R_{(\lambda)}$ can be calculated using the following equation:

$$R_{(\lambda)} = r\_Si(\lambda) \times (R_{s(\lambda)} - R_{b(\lambda)}) / (R_{r(\lambda)} - R_{b(\lambda)})$$

where $r\_Si(\lambda)$ is the absolute reflectance of silicon, which is known.

In step 635, processor 260 can save the results and then grade each chip for its quality in terms of light extraction efficiency. For example, in one embodiment, a threshold can be set (by system or user) to reject a chip when its average reflectance is below the threshold. In step 636, processor 260 can command XY stage 610 to move to an unload position where the operator can unload industrial sample 621, thereby finishing sequence 600 for one industrial sample.

FIG. 7 illustrates another 3D surface measurement system 700 in which processor 260 can automatically provide all three modes of operation, i.e. regular 3D imaging, polarized light 3D imaging, and surface reflectance measurement. In this embodiment, processor 260 is coupled to a linear slider 707, a polarizer assembly 715, an analyzer assembly 770, and a turret 705 to provide motorized control of those components (wherein linear slider 707, polarizer assembly 715, analyzer assembly 770, and turret 705 have the same functionality described above for linear slider 107, a polarizer assembly 115, an analyzer assembly 270, and a turret 205, respectively). For example, when operating in regular 3D imaging mode, processor 260 commands polarizer assembly 715 and analyzer assembly 770 to pull the polarizer and the analyzer out of the illumination light path. Motorized turret 705 can place a lower magnification objective such as 5× in the illumination light path. In one preferred embodiment, a deskew operation (e.g. step 631, FIG. 6B) can be performed after the wafer is loaded. After deskew, motorized turret 705 can switch to a high magnification objective, such as 100×. Then, system 700 can perform an autofocus operation at each pre-defined measurement spot. A detailed description of an autofocus operation is disclosed in U.S. patent application Ser. No. 13/172,686, entitled "3D Microscope And Methods Of Measuring Patterned Substrates", filed on Jun. 29, 2011, and incorporated by reference herein. After autofocus, system 700 can acquire a 3D image of the surface, calculate surface roughness parameters, and save the resulting data. This process can be repeated until every chip location on the map is visited and data collected.

When system 700 operates in the polarized light 3D imaging mode, processor 260 commands polarizer assembly 715 and analyzer assembly 770 to be inserted into the illumination light path. Motorized turret 705 places a lower magnification objective such as 5× in the illumination light path. A deskew process is performed after the wafer is loaded. After deskew, motorized turret 705 then switches to a high magnification objective such as 100×. Stage 610 is moved to the first measurement spot. System 700 performs an autofocus and then automatically adjusts motorized thumb knob 715B so that image contrast is maximized. After that, system 700 carries out an analysis sequence by visiting each pre-defined measurement location. At each location, system 700 performs an autofocus, acquires a 3D image of the surface, calculates surface roughness parameters, and saves data. This process can be repeated until every chip location on the map is visited and data collected.

When system 700 operates in surface reflectance measurement mode, processor 260 commands polarizer assembly 715 and analyzer assembly 770 to be pulled out of the illumination light path. Motorized turret 705 places the lowest magnification objective in the illumination light path. A deskew process is performed after the wafer is loaded. After that, system 700 carries out a sequence similar to the one described earlier during the discussion of FIG. 6B.

The above-described systems and techniques can advantageously provide HBLED manufacturers with non-destructive solutions for monitoring PEC roughening process. These systems and techniques are easy to use, fast in throughput, and relatively inexpensive to implement. Moreover, the disclosed method of surface reflectance spectrum analysis of this invention correlates well with final LED light extraction efficiency.

Although the above-described systems and techniques can be used for monitoring PEC roughened LED chip surfaces, those skilled in the art will appreciate that those systems and techniques can also be applied to other types of sample surfaces, and therefore are within the scope of the present invention.

The invention claimed is:
1. A measurement system for monitoring a light emitting diode (LED) chip surface roughening process, the measurement system comprising:
   an objective lens;
   a reflective illuminator configured to run reflectance measurements;
   a vertical positioning means to adjust a distance between the objective lens and an industrial sample, the industrial sample including an LED chip;

a horizontal positioning means to move objects in XY plane, the horizontal positioning means configured to hold the industrial sample and a reference sample;

an optical sensor that acquires images of the industrial sample;

a spectrometer that acquires reflectance spectrums of the industrial sample and the reference sample; and a processor that controls the illuminator, the vertical positioning means, the horizontal positioning means, the optical sensor, and the spectrometer, the processor configured to perform deskew, to calculate an average reflectance and an oscillation amplitude from the reflectance spectrums of the industrial sample, and determine a roughness of the industrial sample from the calculated average reflectance and oscillation amplitude.

2. The measurement system of claim 1, wherein the objective lens has 5× or lower magnification.

3. The measurement system of claim 1, wherein the reflective illuminator includes at least one broadband white light LED source.

4. The measurement system of claim 1, wherein the vertical positioning means includes a motorized Z stage.

5. The measurement system of claim 1, wherein the horizontal positioning means includes a motorized XY stage.

6. The measurement system of claim 1, wherein the reference sample is a polished bare silicon substrate.

7. The measurement system of claim 1, wherein the optical sensor includes a CCD camera.

8. The measurement system of claim 1, wherein the spectrometer is configured to collect reflectance data between 430 nm and 750 nm.

9. The measurement system of claim 1, wherein the processor is part of a PC.

10. A method of forming a system for monitoring a light emitting diode (LED) chip surface roughening process, the method comprising:

providing an objective lens;

providing a reflective illuminator configured to run reflectance measurements;

providing a vertical positioning means to adjust a distance between the objective lens and an industrial sample, the industrial sample including an LED chip;

providing a horizontal positioning means to move objects in an XY plane, the horizontal positioning means configured to hold the industrial sample and a reference sample;

providing an optical sensor that acquires images of the industrial sample;

providing a spectrometer that acquires reflectance spectrums of the industrial sample and the reference sample; and providing a processor that controls the illuminator, the vertical positioning means, the horizontal positioning means, the optical sensor, and the spectrometer, the processor configured to perform deskew, to calculate an average reflectance and an oscillation amplitude from the reflectance spectrums of the industrial sample, and determine a roughness of the industrial sample from the calculated average reflectance and oscillation amplitude.

11. The method of claim 10, wherein providing the objective lens includes setting the objective lens at 5× or lower magnification.

12. The method of claim 10, wherein providing the reflective illuminator includes selecting at least one broadband white light LED source for the reflective illuminator.

13. The method of claim 10, wherein providing the vertical positioning means includes selecting a motorized Z stage for the vertical positioning means.

14. The method of claim 10, wherein providing the horizontal positioning means includes selecting a motorized XY stage for the horizontal positioning means.

15. The method of claim 10, wherein providing the optical sensor includes selecting a CCD camera for the optical sensor.

16. The method of claim 10, wherein acquiring the reflectance spectrum includes collecting reflectance data between 430 nm and 750 nm.

17. The method of claim 10, wherein providing the processor includes coupling a PC to the illuminator, the positioning means, the optical sensor, and the spectrometer.

18. A measurement system for monitoring a light emitting diode (LED) chip surface roughening process, the measurement system comprising:

an objective lens;

an illuminator configured to selectively run a surface reflectance measurement mode and at least one of a regular 3D imaging mode and a polarized light 3D imaging mode;

a positioning means to adjust a distance between the objective lens and a sample at a plurality of Z steps;

an optical sensor configured to acquire images of the sample at each Z step;

a spectrometer configured to acquire reflectance spectrums; and a processor that controls the illuminator, the positioning means, the optical sensor, and the spectrometer, the processor configured to calculate an average reflectance and an oscillation amplitude from the reflectance spectrums, and determine a roughness of the industrial sample from the calculated average reflectance and oscillation amplitude.

19. The measurement system of claim 18, wherein the illuminator includes at least one broadband white light LED source.

20. The measurement system of claim 18, wherein the illuminator is configured to switch between the surface reflectance measurement mode, the regular 3D imaging mode, and the polarized light 3D imaging mode during operation.

21. The measurement system of claim 18, wherein the positioning means includes a motorized Z stage.

22. The measurement system of claim 18, wherein the optical sensor includes a CCD camera.

23. The measurement system of claim 18, wherein the spectrometer is configured to collect reflectance data between 430 nm and 750 nm.

24. The measurement system of claim 18, wherein the processor is part of a PC.

25. A method of forming a system for monitoring a light emitting diode (LED) chip surface roughening process, the method comprising:

providing an objective lens;

providing a reflective illuminator configured to run surface reflectance measurements;

providing a positioning means to adjust a distance between the objective lens and a sample;

providing an optical sensor that acquires images of the sample;

providing a spectrometer that acquires reflectance spectrums; and providing a processor that controls the illuminator, the positioning means, the optical sensor, and the spectrometer, the processor configured to calculate average reflectance and oscillation amplitude from the reflectance spectrum, and determine a roughness of the industrial sample from the calculated average reflectance and oscillation amplitude.

26. The method of claim 25, wherein providing the objective lens includes setting the objective lens to 5× or lower magnification.

27. The method of claim 25, wherein providing the reflective illuminator includes selecting at least one broadband white light LED source for the reflective illuminator.

28. The method of claim 25, wherein providing the positioning means includes selecting a motorized Z stage for the positioning means.

29. The method of claim 25, wherein providing the optical sensor includes selecting a CCD camera for the optical sensor.

30. The method of claim 25, wherein acquiring the reflectance spectrum includes collecting reflectance data between 430 nm and 750 nm.

31. The method of claim 25, wherein providing the processor includes coupling a PC to the illuminator, the positioning means, the optical sensor, and the spectrometer.

32. A measurement system for monitoring a light emitting diode (LED) chip surface roughening process, the measurement system comprising:
   a turret including an objective lens;
   a reflective illuminator configured to selectively run a surface reflectance measurement mode and a polarizing light 3D imaging mode;
   a vertical positioning means to adjust a distance between the objective lens and an industrial sample at a plurality of Z steps;
   a horizontal positioning means to move objects in XY plane, the horizontal positioning means configured to hold the industrial sample and a reference sample;
   an optical sensor that acquires images of the industrial sample at each Z step;
   a spectrometer that acquires reflectance spectrums of the industrial sample and the reference sample; and
   a processor that controls the turret, the illuminator, the vertical positioning means, the horizontal positioning means, the optical sensor, and the spectrometer, the processor configured to perform deskew, to calculate an average reflectance and an oscillation amplitude from the reflectance spectrums, and determine a roughness of the industrial sample from the calculated average reflectance and oscillation amplitude.

33. The measurement system of claim 32, wherein the objective lens has 5× or lower magnification in the surface reflectance measurement mode.

34. The measurement system of claim 33, wherein the objective lens has 100× or higher magnification in the polarizing light 3D imaging mode.

35. The measurement system of claim 33, wherein the reflective illuminator includes at least one broadband white light LED source.

36. The measurement system of claim 33, wherein the reflective illuminator is configured to switch between the surface reflectance measurement mode and the polarizing light 3D imaging mode automatically.

37. The measurement system of claim 33, wherein the vertical positioning means includes a motorized Z stage.

38. The measurement system of claim 33, wherein the horizontal positioning means includes a motorized XY stage.

39. The measurement system of claim 33, wherein the reference sample is a polished bare silicon substrate.

40. The measurement system of claim 33, wherein the optical sensor includes a CCD camera.

41. The measurement system of claim 33, wherein the spectrometer is capable of collecting reflectance data between 430 nm and 750 nm.

42. The measurement system of claim 33, wherein the processor is part of a PC.

* * * * *